(12) United States Patent
Ho et al.

(10) Patent No.: US 8,258,291 B2
(45) Date of Patent: Sep. 4, 2012

(54) PROCESS FOR THE PREPARATION OF SUCRALOSE BY THE CHLORINATION OF SUGAR WITH TRIPHOSGENE (BTC)

(75) Inventors: David Losan Ho, Los Angeles, CA (US); Wan Zhenghao, Wyuishan (CN)

(73) Assignee: Mamtek International Limited, Hong Kong (CN)

( * ) Notice: Subject to any disclaimer, the term of this patent is extended or adjusted under 35 U.S.C. 154(b) by 560 days.

(21) Appl. No.: 11/552,789

(22) Filed: Oct. 25, 2006

(65) Prior Publication Data

US 2008/0103298 A1 May 1, 2008

(51) Int. Cl.
*C07H 1/00* (2006.01)
*C07H 5/02* (2006.01)

(52) U.S. Cl. ........................ 536/124; 536/122

(58) Field of Classification Search .................. 536/122, 536/124
See application file for complete search history.

(56) References Cited

U.S. PATENT DOCUMENTS

| | | | |
|---|---|---|---|
| 3,072,725 A | 1/1963 | Clemens | |
| 4,380,476 A * | 4/1983 | Mufti et al. .................. | 127/46.3 |
| 4,977,254 A | 12/1990 | Homer et al. | |
| 4,980,463 A | 12/1990 | Walkup et al. | |
| 5,498,709 A | 3/1996 | Navia | |
| 2002/0173645 A1 | 11/2002 | Luke | |
| 2003/0171575 A1 | 9/2003 | Catani et al. | |
| 2006/0205936 A1 | 9/2006 | Jia et al. | |
| 2008/0103295 A1 | 5/2008 | Ho et al. | |

FOREIGN PATENT DOCUMENTS

| | | |
|---|---|---|
| JP | 03-148244 | 6/1991 |
| WO | 2004104016 A1 | 12/2004 |
| WO | 2007/052304 A2 | 5/2007 |
| WO | 2008/015694 A2 | 2/2008 |
| WO | 2008052077 A2 | 5/2008 |

OTHER PUBLICATIONS

Eckert et al. Angewandte Chemie Int. Ed. Engl. 1987, 26(9), p. 894-895.*
International Search Report for International Application No. PCT/US07/82422 dated May 16, 2008, 2 pages.
International Search Report for International Application No. PCT/US07/82424 dated May 20, 2008, 2 pages.
Yamaguchi, T., "Recent Progress in Solid Superacid," Applied Catalysis 1990, 61:1-25.
Jiang et al., Preparation and properties of A1-PILC supported SO42-/TiO2 superacid catalyst, Journal of Molecular Catalysis A: Chemical 213 (2004) 231-234.
United States Patent and Trademark Office, International Search Report and Written Opinion for PCT/US09/51595, dated Sep. 14, 2009.
United States Patent and Trademark Office, International Search Report and Written Opinion for PCT/US09/51588, dated Sep. 15, 2009.

* cited by examiner

*Primary Examiner* — Shaojia Anna Jiang
*Assistant Examiner* — Jonathan S Lau

(57) ABSTRACT

In one embodiment of the invention a method to prepare sucralose-6-acylate through chlorinating sucrose-6-acylate by BTC in the process of sucralose preparation is disclosed. In this embodiment a Vilsmeier reagent is firstly prepared below 0° C. by dissolving BTC in DMF or in component solvent, containing DMF, toluene, dichloroethane, chloroform and carbon tetrachloride. Consequently, sucrose-6-ester was chlorinated by Vilsmeier reagent. BTC can also be dissolved in one or several organic solvent such as toluene, dichloroethane, chloroform and carbon tetrachloride, and added to a DMF solution of sucrose-6-acylate for chlorination. Sucralose was prepared through de-esterifying the obtained sucralose 6-ester using sodium methoxide/methanol or sodium ethoxide/ethanol.

24 Claims, No Drawings

PROCESS FOR THE PREPARATION OF SUCRALOSE BY THE CHLORINATION OF SUGAR WITH TRIPHOSGENE (BTC)

FIELD OF THE INVENTION

The present invention relates to a method of making sucralose.

BACKGROUND OF THE INVENTION

The monoester method has been used in the synthesis of sucralose. Converted to sucrose-6-ester from sucrose, sucralose-6-ester is generated through chlorinating sucrose-6-ester. Sucralose is prepared through alcoholysis of sucralose-6-ester by using sodium methoxide/methanol or sodium ethoxide/ethanol. The commonly used chlorinating reagent is a Vilsmeier reagent, which was usually prepared through reacting DMF with phosgene or with thionyl chloride. A major drawback of such methods is the amount of sulfur dioxide emitted through chlorination which leads to increase treatment procedures and requirements for equipment. Further because phosgene is a strongly toxic gas, it is not suitable to store, transport and use.

Accordingly there is a need in the art for an improved method making sucralose at high yield with less toxic by products.

SUMMARY OF THE INVENTION

In one embodiment of the present invention, a method for the preparation of a sucralose from sucrose-6-ester is provided comprising using BTC to generate a Vilsmeier reagent for chlorination wherein the Vilsmeier reagent is generated by dissolving BTC in DMF and wherein the mole equivalents of BTC:sucrose-6-ester is in the range of about 2.8:1 to 3.5:1.

DETAILED DESCRIPTION

The following description of the invention is intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

In one embodiment of the present invention a method for the chlorination of sugars to produce chlorodeoxy derivatives, and in particular to the chlorination of sugars and sugar derivatives in the preparation of chlorodeoxy sugar sweeteners such as sucralose (4,1',6'-trichloro-4,1',6'-trideoxygalactosucrose) is provided.

In one aspect of the invention, a Vilsmeier reagent is prepared by adding a chlorination reagent to a solvent comprising DMF or DMF and one or a mixture of other organic solvent such as toluene, cyclohexane, dichloroethane, chloroform and carbon tetrachloride. Sucrose-6-ester is dissolved into solvent. Both the Vilsmeier reagent and the DMF solution of sucrose-6-ester are chilled to below 0° C. before mixing. The Vilsmeier reagent is then added to DMF solution of sucroses-6-ester dropwise so that the reaction temperature is kept below 5° C. The reaction mixture is stirred at a temperature below 5° C. for 2 h after the addition of Vilsmeier reagent is complete. The reaction mixture is then warmed up at room temperature and maintained at room temperature for another 2 h. The reaction is then heated for 2-3 h to reach 110° C. and refluxed at 110° C. for 3 h. Afterwards, the reaction mixture is cooled to room temperature naturally. The pH of the reaction mixture is first adjusted to 8-9 by ammonia hydroxide/methanol solution (1:1), and then to 6-7 by glacial acetic acid. After removing most of the solvent by distillation under reduced pressure, the sucrose-6-ester is extracted by ethyl acetate and water. The combined organic phase is distilled under reduced pressure to afford sucralose-6-ester syrup. The sucralose-6-ester is then converted to sucralose by de-esterification using sodium methoxide/methanol or sodium ethoxide/ethanol.

In another aspect of the invention, a chlorination reagent can also be dissolved in one or several organic solvents, such as toluene, cyclohexane, dichloroethane, chloroform and carbon tetrachloride, before it is added into the DMF solution of sucrose-6-acetate with the same protocol as described above.

The chlorination reagent can be selected from a group consisting of triphenylhydrazine, phosphoric chloride, thionyl chloride, phosgene, oxalyl chloride. It is preferably triphosgene (Bis(trichloromethyl) carbonate, BTC). BTC is safe and convenient to use, and it causes no pollution and corrosion concerns.

The concentration of the sucrose-6-ester is preferably from 0.1 to 0.11 mol/L.

The mole equivalent (ME) of chlorination reagent comparing to sucrose-6-ester is from 2.8 to 3.5.

The reaction can be carried out under vacuum to avoid the oxidation of the reaction mixture by oxygen in ambient atmosphere. Alternatively undesired oxidation may be avoided by refluxing the reaction mixture in the presence of a low-boiling-point organic solvent such as cyclohexane, dichloroethane, ethyl acetate, chloroform and carbon tetrachloride.

EXAMPLES

Example 1

Chlorination of Sucrose-6-Ester with BTC Dissolved in DMF

Sucrose-6-acetate (30 g, 0.08 mol) was dissolved in DMF (300 mL) and maintained at a temperature below 0° C. BTC (80 g, 0.27 mol) was gently added to DMF (500 mL) at a temperature below 0° C. to prepare the Vilsmeier reagent. The Vilsmeier reagent was added to the DMF solution of sucrose 6-acetate slowly to keep the reaction temperature below 5° C. The reaction was stirred at a temperature below 5° C. for 2 h and another 2 h at ambient temperature. The reaction mixture was then was heated to 110° C. slowly and refluxed at 110° C. for 3 h. After the reaction was completed, the reaction mixture was allowed to cool to ambient temperature naturally. The reaction mixture was neutralized with ammonia hydroxide/methanol (1:1, 400 mL) to reach pH 8-9. After the reaction mixture was stirred for 5 min at ambient temperature, the pH of the reaction was further adjusted to 6-7 by adding glacial acetic acid. Then most of the solvent was removed by distillation under reducing pressure. Distilled water (100 mL) and ethyl acetate (500 mL) were added to the remaining solution. The mixture was stirred for 1 h at ambient temperature and filtered. The filter cake was washed with ethyl acetate (150 mL). The water phase of the filtrate was extracted with ethyl acetate (3×200 mL). The combined organic phase was washed with brine (2×100 mL) and then concentrated to around 400 mL by distillation under reduced pressure at a temperature below 60° C. The remaining solution was decolored by activated charcoal (10 g), filtered and concentrated into syrup (40 g, containing 20 g (0.045 mol) sucralose 6-acetate, yield is 56%).

Example 2

Chlorination of Sucrose-6-Ester with BTC Dissolved in Toluene

The reaction was carried out following the same protocol as example 1 except that a toluene solution of BTC was added directly to the DMF solution of sucrose-6-acetate (30 g, 0.08 mol) to initiate the chlorination reaction. The toluene solution of BTC was prepared by dissolving BTC (80 g, 0.27 mol) in cooled toluene (400 mL) below 0° C. The product was a syrup containing 22 g sucralose 6-acetate (0.05 mol) with a yield of 62.5%.

Example 3

Preparation of Sucralose from Sucralose-6-Acetate

Twenty percent sodium methoxide/methanol (4 g, 0.015 mol NaOMe) solution was added to a 15° C. methanol (100 mL) solution of Sucralose 6-acetate (10 g, 0.023 mol). The mixture was stirred for 5 h at room temperature. The reaction was neutralized and filtered through hydrogen strong acidic ion exchange resin, which was cleansed by methanol. The filtrate was concentrated under reduced pressure below 30° C., to a soft foam. The foam was dissolved in distilled water (100 mL), and the solution was extracted by ethyl acetate (50 mL). The aqueous phase was then decolored with activated charcoal (0.5 g), filtered to remove the activated charcoal and washed with distilled water (2×300 mL). The filtrate was concentrated to syrup by distillation under reduced pressure at room temperature. Distilled water (8 mL) was added to dissolve the syrup at 80° C. After the solution was cooled to below 20° C., crystal seeds were added to the solution. The formed crystals were filtered and washed by small amount of cold water, dried, then dried in crystallizing dish under reduced pressure at 45-50° C. to produce sucralose (5 g, 0.013 mol, yield 86%).

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

What is claimed is:

1. A method for the preparation of sucralose from sucrose-6-ester comprising:
    generating a Vilsmeier reagent by dissolving bis(trichloromethyl) carbonate (BTC) in DMF;
    contacting the Vilsmeier reagent with sucrose-6-ester to form a first mixture; and
    conducting the chlorination reaction under a vacuum to avoid oxidation.

2. The method of claim 1, wherein the Vilsmeier reagent was prepared by dissolving BTC in DMF with one or more organic solvents.

3. The method of claim 2, wherein the organic solvent is selected from a group consisting of cyclohexane, toluene, dichloroethane, chloroform, and carbon tetrachloride.

4. The method of claim 1 wherein the first mixture further comprises ethyl acetate.

5. The method of claim 1, wherein the mole equivalents of BTC:sucrose-6-ester is in the range of 2.8:1 to 3.5:1.

6. The method of claim 1, further comprising:
    cooling the Vilsmeier reagent to below 0° C. before contacting the Vilsmeier reagent with sucrose-6-ester;
    controlling the reaction temperature under 5° C. as the Vilsmeier reagent is contacting with sucrose-6-ester to form the first mixture; and
    warming the first mixture to room temperature.

7. The method of claim 6 further comprising:
    maintaining the first mixture at the room temperature for 3 h to form a second mixture;
    heating the second mixture to 110° C.; and
    refluxing the second mixture at a temperature of 110° C. for 3 h.

8. A method for the preparation of sucralose from sucrose-6-ester comprising:
    generating a Vilsmeier reagent by dissolving bis(trichloromethyl) carbonate (BTC) in DMF;
    providing a first solution comprising sucrose-6-ester;
    combining the Vilsmeier reagent and the first solution to form a first mixture; and
    conducting the chlorination reaction under a vacuum to avoid oxidation.

9. The method of claim 8 further comprising cooling the Vilsmeier reagent and the first solution below about 0° C. prior to combining the Vilsmeier reagent and the first solution.

10. The method of claim 9 wherein the step of combining the Vilsmeier reagent and the first solution comprises maintaining the temperature of the first mixture below about 5° C. for a first time period.

11. The method of claim 10 further comprising refluxing the first mixture at an elevated temperature following the first time period.

12. The method of claim 11 wherein the elevated temperature is at least 100° C.

13. The method of claim 11 wherein the mole equivalents of BTC:sucrose-6-ester in the first mixture is in the range of about 2.8:1 to 3.5:1.

14. The method of claim 12 wherein the mole equivalents of BTC:sucrose-6-ester in the first mixture is in the range of about 2.8:1 to 3.5:1.

15. The method of claim 8 wherein generating a Vilsmeier reagent by dissolving bis(trichloromethyl) carbonate in DMF further comprises dissolving bis(trichloromethyl) carbonate in a mixture comprising DMF and at least one other organic solvent.

16. The method of claim 15 wherein at least one other organic solvent is selected from the group consisting of cyclohexane, toluene, dichloroethane, chloroform, and carbon tetrachloride.

17. The method of claim 8 wherein the first mixture further comprises ethyl acetate.

18. A method for the preparation of sucralose from sucrose-6-ester comprising:
    generating a Vilsmeier reagent by dissolving bis(trichloromethyl) carbonate (BTC) in DMF;
    providing a first solution comprising sucrose-6-ester;
    cooling the Vilsmeier reagent and the first solution below about 0° C.;
    combining the Vilsmeier reagent and the first solution to form a first mixture wherein the first mixture is maintained at a temperature below about 5° C. for a first time period and wherein the mole equivalents of BTC:sucrose-6-ester in the first mixture at the start of the first time period is in the range of about 2.8:1 to 3.5:1; and refluxing the first mixture at an elevated temperature following the first time period for a second time period, wherein the chlorination reaction is conducted under a vacuum to avoid oxidation.

19. The method of claim 18 further comprising:

cooling the first mixture to a temperature below the elevated temperature following the second time period; and adjusting the pH of the first mixture so that the final pH of the first mixture is 6-7.

20. The method of claim 18 further comprising stirring the first mixture during the first time period, wherein the first time period is at least about 2 hours.

21. The method of claim 19 wherein the second time period is at least about 3 hours.

22. The method of claim 18 wherein generating a Vilsmeier reagent by dissolving bis(trichloromethyl) carbonate in DMF further comprises dissolving bis(trichloromethyl) carbonate in a mixture comprising DMF and at least one other organic solvent.

23. The method of claim 22 wherein at least one other organic solvent is selected from the group consisting of cyclohexane, toluene, dichloroethane, chloroform, and carbon tetrachloride.

24. The method of claim 18 wherein the first mixture further comprises ethyl acetate.

* * * * *